United States Patent [19]
Ridenour

[11] Patent Number: 6,113,539
[45] Date of Patent: Sep. 5, 2000

[54] PHYSICAL MONITORING SYSTEM FOR FEEDLOT ANIMALS

[75] Inventor: Ken W. Ridenour, Amarillo, Tex.

[73] Assignee: K.E.R. Associates, Inc., Amarillo, Tex.

[21] Appl. No.: 09/239,071

[22] Filed: Jan. 27, 1999

[51] Int. Cl.$^7$ ............................................. A61B 5/00
[52] U.S. Cl. .................. 600/300; 600/309; 600/481; 128/903
[58] Field of Search .................... 600/300, 301, 600/304, 305, 310, 481, 508, 545, 551; 128/903

[56] References Cited

U.S. PATENT DOCUMENTS 4,411,274  10/1983  Wright ..................................... 128/903
4,630,613  12/1986  Dennis ..................................... 128/903

*Primary Examiner*—Eric F. Winakur
*Attorney, Agent, or Firm*—Howrey Simon Arnold & White, LLP

[57] ABSTRACT

The health and welfare of feedlot animals are observed with a monitoring system that is simple to implement and easily expandable depending on the feedlot operator's need. The monitoring system uses a sleeve that is removably attached to an appendage of the animal, such as its tail. The sleeve contains a biosensor for sensing the animal's physiological parameters and a microprocessor for processing these sensed parameters. When the animal's monitored physiological parameter is out of a predetermined "healthy" range, the microprocessor activates an alarm to alert the feedlot operator of a potential health problem for that particular animal. The sleeve can optionally contain a transmitter so that the sensed physiological parameters can be transmitted to a base station. Additionally, the monitoring system can be expanded to include animal tracking capability so that the animal's feeding and watering habits can also be monitored at the base station. A GPS-system or a tag-based system may be used to track the animals.

42 Claims, 11 Drawing Sheets

PHYSICAL MONITORING SYSTEM FOR FEEDLOT ANIMALS

FIELD OF THE INVENTION

The present invention relates to monitoring systems in general, and more specifically to physical monitoring systems for feedlot animals and a method for using the same.

BACKGROUND OF THE INVENTION

In the cattle business and in particular, the feedlot industry, forty to fifty thousand head of cattle are located at any given time in a typical feedlot, with an average pen space of 150–250 square feet per animal. When animals are maintained in such close quarters, it is necessary to diligently monitor the health of the animals so that as soon as any particular animal indicates symptoms of sickness, that animal can be removed and treated. Presently, most feedlots utilize a "pen rider" who rides on a horse into the individual pens and looks for animals that appear lethargic or demonstrate some other indication of sickness or poor health. As can be expected, this system is only as good as the particular person's ability to observe such characteristics. Also, these characteristics may only become visible after the sickness has substantially progressed. It would be a tremendous benefit to the animal owner to be able to timely monitor certain physiological parameters of each animal and be able to use these parameters to identify an animal in the early stages of sickness. These physiological parameters typically would include the temperature and pulse rate of the animal. Additionally, the frequency of feed and water intake of an animal are other good indicators of the animal's well-being.

Various patents have attempted to allow the user to monitor a farm animal's temperature in order to allow early detection of fever or illness. Most of these devices are designed to be implanted into the animal or inserted into a bodily canal. These devices are hard to use because they are either difficult to insert or are easily dislodged or expelled by the animal. Furthermore, implanting the devices via an incision itself creates a risk of infection and illness.

U.S. Pat. No. 4,865,044 provides a device that is implanted in the cow's ear or attached to the ear canal of the animal. The device includes a thermistor to detect the internal temperature of the cow, and also provides means for compensating for ambient temperature when the device has fallen out of the animal's ear or ear canal.

Similarly, U.S. Pat. No. 4,854,328 discloses a capsule, containing a temperature sensor and a transmitter, that is implanted into an animal, such as at the base of the skull. A receiver is placed on a tag that is attached to the animal's ear, much like an earring. The ear tag has an indicator that provides a warning when the animal's temperature is out of a predetermined range.

U.S. Pat. No. 4,399,821 discloses implantable devices that would allow for monitoring one or more physiological parameters of free moving animals.

U.S. Pat. No. 3,893,111 also discloses a capsule that is embedded into an animal to allow for remote monitoring of the animal's temperature.

U.S. Pat. No. 3,781,837 provides a device that consists of an electronic package that is fastened around the animal's neck and that is also connected to a thermistor sensing element which is implanted in one of the ear canals of the animal. When the temperature sensor indicates that the animal's inner temperature is out of a predetermined range, an audio, visual, or radio frequency alarm is provided to indicate that the animal should receive treatment.

Other patents have focused on monitoring and measuring the feed consumption and weight change of animals. In U.S. Pat. No. 3,465,724, an animal wears a device that is sensed by the feeder and opens the feed bin if it is the right animal. The system monitors the feeding times and amounts consumed by the animal.

U.S. Pat. No. 3,541,995 discloses a feed monitoring system that includes an interrogator and a transponder that allows for recognition of individual animals. The transponder measures the dwell time of the animal at the feed station and dispenses a preprogrammed feed amount for that animal to control its feed intake. Only when another animal enters the feed zone will additional feed be discharged at that station.

U.S. Pat. No. 3,929,277 discloses another animal feed monitoring system that senses an identification tag, attached to the animal's ear or embedded under its skin, and weighs the amount of feed consumed by the animal. The information gathered on each animal is stored within a memory bank for later use.

U.S. Pat. No. 4,532,892 discloses an animal feeding and monitoring system that includes an electronic tag attached around a cow's neck for identifying specific animals and then controlling the amount of feed that is dispensed to that particular animal.

U.S. Pat. No. 4,617,876 discloses a monitoring system comprising an ear tag and a scale in a feed and/or water stall. Only one cow at a time can enter the stall, and is automatically weighed as it is drinking or eating in the stall.

However, none of these systems provides for a monitoring system that is simple to use, that is nonintrusive to the animal, that has the flexibility of providing different types of information depending on the user's particular need.

SUMMARY OF THE INVENTION

The present invention provides a system for monitoring feedlot animals, wherein a monitoring sleeve is removably attached around the upper end of an animal's tail and includes an insertable instrument pack contained within a sealable pouch. One or more biosensors capable of measuring the desired physiological parameters of the animal are attached to the inner surface of the sleeve. These biosensors are operatively connected to a microprocessor housed within the instrument pack. The biosensors measure the animal's physiological parameters and provide corresponding signals to the microprocessor. The microprocessor analyzes the information and activates an alarm when the physiological parameters of the animal meet certain criteria in order to allow quick and easy identification of animals with potential health problems.

The instrument pack may optionally include a transmitter to transmit signals relating to the animal's measured physiological parameters to a base station. The transmitted signal includes an identifying number to identify the particular animal from which the physiological measurements were taken.

In addition to monitoring an animal's physiological parameters for an early indication of sickness, the monitoring system can optionally also monitor the animal's feed and/or water intake as another health indicator. This may be accomplished by monitoring the geographic location of the animal to determine the frequency and amount of time spent at or near the feed bunks and water troughs. The instrument pack could include a small global positioning system (GPS) receiver for determining the geographic location of the animal and a transmitter to send this information to the base station. As an alternative to a GPS based system, a tag-based system could be used to cause a signal to be transmitted to the base station when the animal bearing a tag passes near a tag-interrogator mounted adjacent to a feed bunk or water trough. Yet another option to determine an animal's location for purposes of calculating feed and/or water intake is to use a system of multiple receivers in the feedlot area. These receivers monitor transmissions by the instrument packs and relay the transmissions or the arrival times of the transmissions near the base station. The base station then uses time difference of arrival techniques to locate the animal.

These and other features, and advantages, will be more clearly understood from the following detailed description taken in conjunction with the accompanying drawings. It is important to point out that the illustrations may not necessarily be drawn to scale, and that there may be other embodiments of the present invention which are not specifically illustrated. Furthermore, as many of the figures illustrate the same or substantially similar elements, like reference numerals will be used to designate elements that are the same or substantially similar in either shape or function.

DETAILED DESCRIPTION OF A PREFERRED EMBODIMENT

The present invention involves a flexible and expandable system for monitoring the physical condition of animals, for example cattle, that are maintained in a feedlot environment. Practice of the present invention is particularly well-suited for a feedlot operator who desires to monitor and track incoming cattle for a limited amount of time, since incoming cattle are prone to shipping stress and may have impaired immune systems. In its simplest form, the present invention provides a mechanism to measure and monitor an animal's physiological parameters, such as its temperature and pulse rate. This mechanism is embodied in a monitoring sleeve that is removably attached to an appendage of the animal, such as around the upper end of the animal's tail. Since feedlots typically maintain cattle, the discussion of the various preferred embodiments of the invention and the illustrations use cattle as exemplary animals. However, it should be understood that practice of the invention is in no way limited to monitoring cattle but rather that the invention is applicable for use on other animals requiring monitoring.

Figure 1:
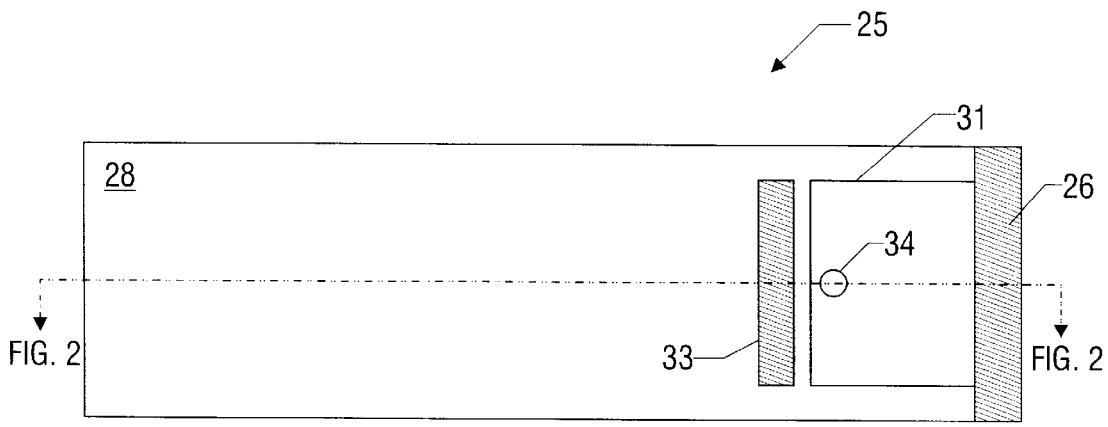
FIG. 1 illustrates, in a top view, a removable sleeve containing an instrument pack, in accordance with a first embodiment of the present invention.
Figure 2:
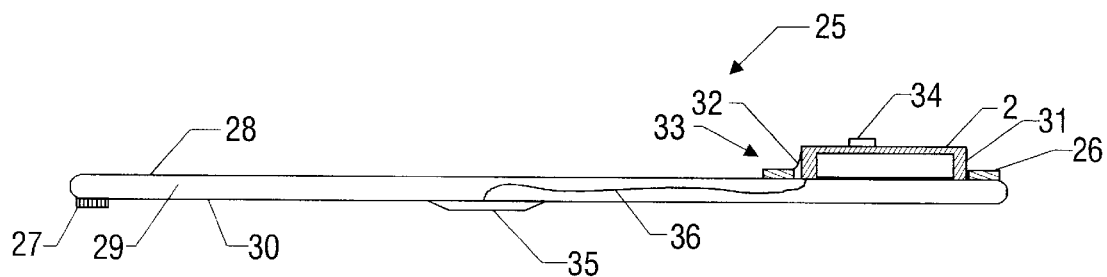
FIG. 2 illustrates, in a cross-sectional view along line 2—2, the removable sleeve of FIG. 1, further showing biosensors and a sealable pouch for carrying and protecting the instrument pack.
Figure 3:
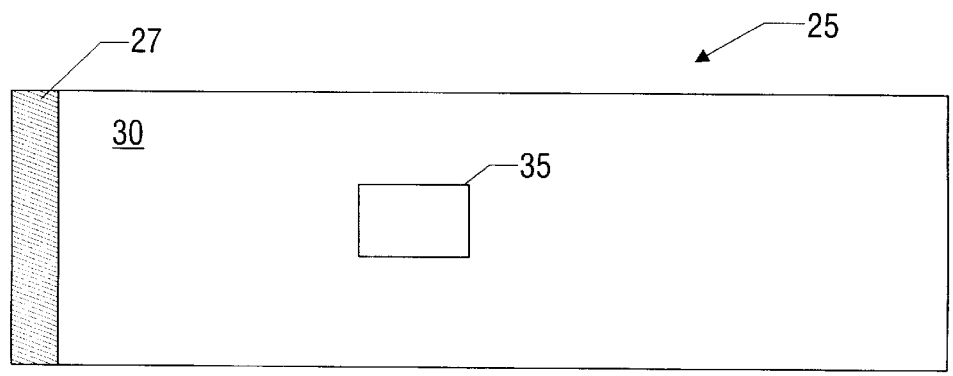
FIG. 3 illustrates a bottom view of the removable sleeve of FIG. 1.
Figure 4:
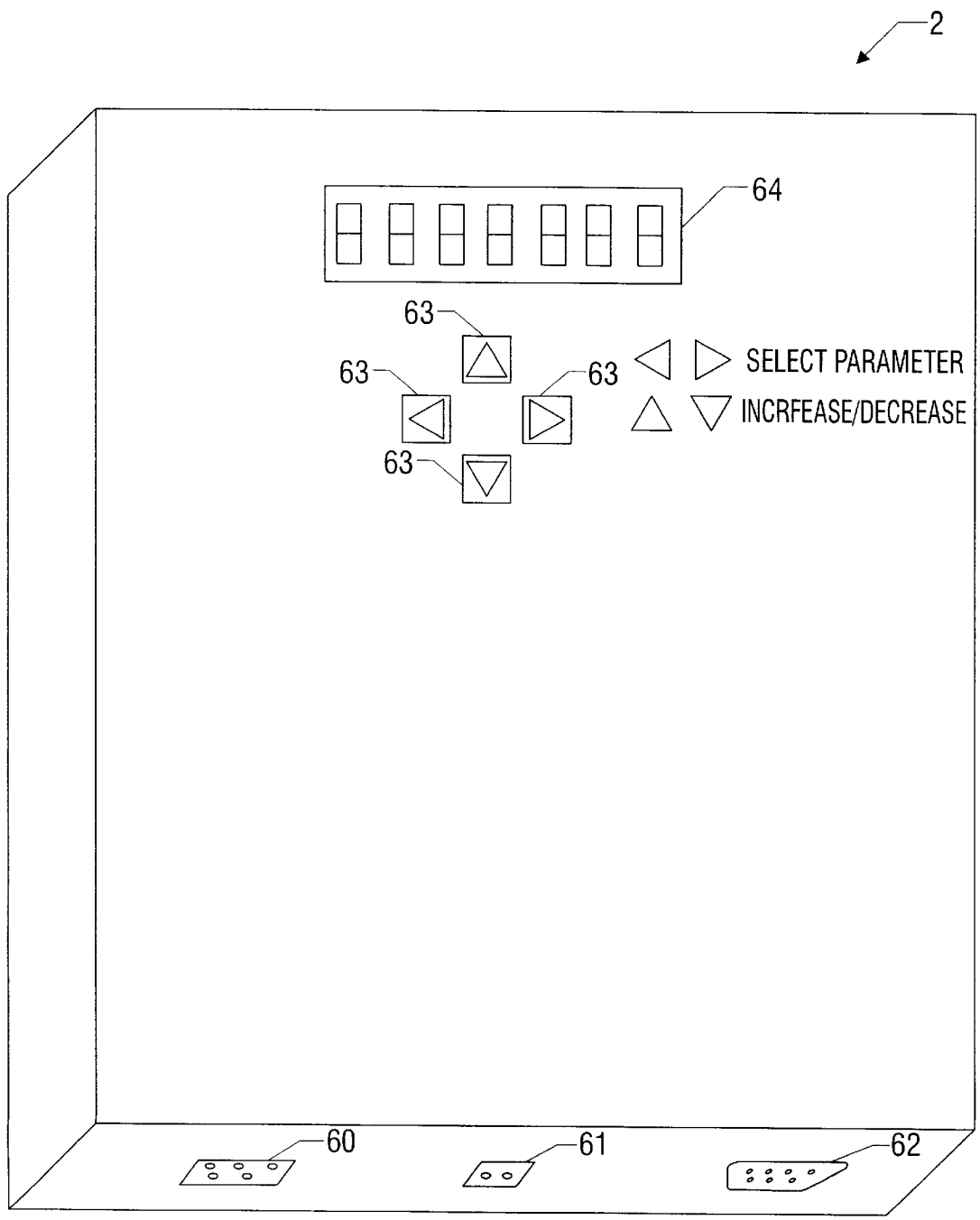
FIG. 4 illustrates an exemplary exterior design of the instrument pack with electrical connectors and an optional user interface.

FIGS. 1–3 illustrate the design of a monitoring sleeve 25 that is suitable for use in all of the embodiments of the present invention. The sleeve 25 has an outer surface 28, an interior 29, and an inner surface 30. As illustrated in FIG. 2, the monitoring sleeve 25 has a pouch 31 to house a separate and insertable instrument pack 2. The pouch 31 is located on the outer surface 28 of the sleeve 25. After the instrument pack 2 is inserted into the pouch 31, the pouch 31 is closed by fastening the pouch's fabric lip 32 to the outer surface 28 of the sleeve 25 via a Velcro® strip 33. Alternatively, snaps, hooks, or other similar fastening means could also be used to close the pouch. A light 34 is located on top of the pouch 31 and may be protected by a housing (not shown) that is attached to the pouch 31. This housing may be sewn on or glued to the pouch and should be clear so that the light may be seen. The light may be incandescent, fluorescent, a light emitting diode (LED), a xenon strobe, or any other suitable light producing device. The light 34 is connected to the instrument pack 2 via an electrical connector 61 which is illustrated in FIG. 4. The connection may be made before or after the instrument pack 2 is inserted into the pouch 31.

As further illustrated in FIG. 2, one or more biosensors 35 are affixed to the inner surface 30 of the monitoring sleeve 25 and are connected via electrical wires 36 embedded within the interior 29 of the sleeve 25 to a data port 60 (see FIG. 4) on the instrument pack 2. The instrument pack 2 is powered by conventional batteries (not shown) and/or solar cells (not shown) affixed to the sleeve in any generally acceptable conventional manner. These batteries may be replaced whenever the monitoring sleeve is removed from an animal to ensure that the sleeve is sufficiently powered for its purpose.

The pouch 31 and the outer surface 28 of the monitoring sleeve 25 are composed of a material that is preferably weather resistant and excrement resistant for durability. A suitable material for this outer surface 28 is Gore-Tex®. Additionally, it may be desirable to make the outer surface 28 white, lightly colored, or reflective to help minimize radiant solar heating of the monitoring sleeve 25. This may be important if one desires to monitor the animal's temperature as one of the physiological parameters—otherwise, a heated sleeve could skew the temperature reading to trigger a false alarm. The interior 29 of the sleeve 25 may also contain a thermally insulative padding, such as Thinsulate® for example. The additional insulation helps to assure proper measurement of the animal's temperature when the ambient environment is relatively hot or cold. Because the inner surface 30 of the sleeve 25 comes into direct contact with the animal's skin and/or hair during use, the inner surface 30 is preferably composed of a rubberized or similar fabric to resist slippage and twisting of the sleeve around the animal's appendage.

Figure 6:
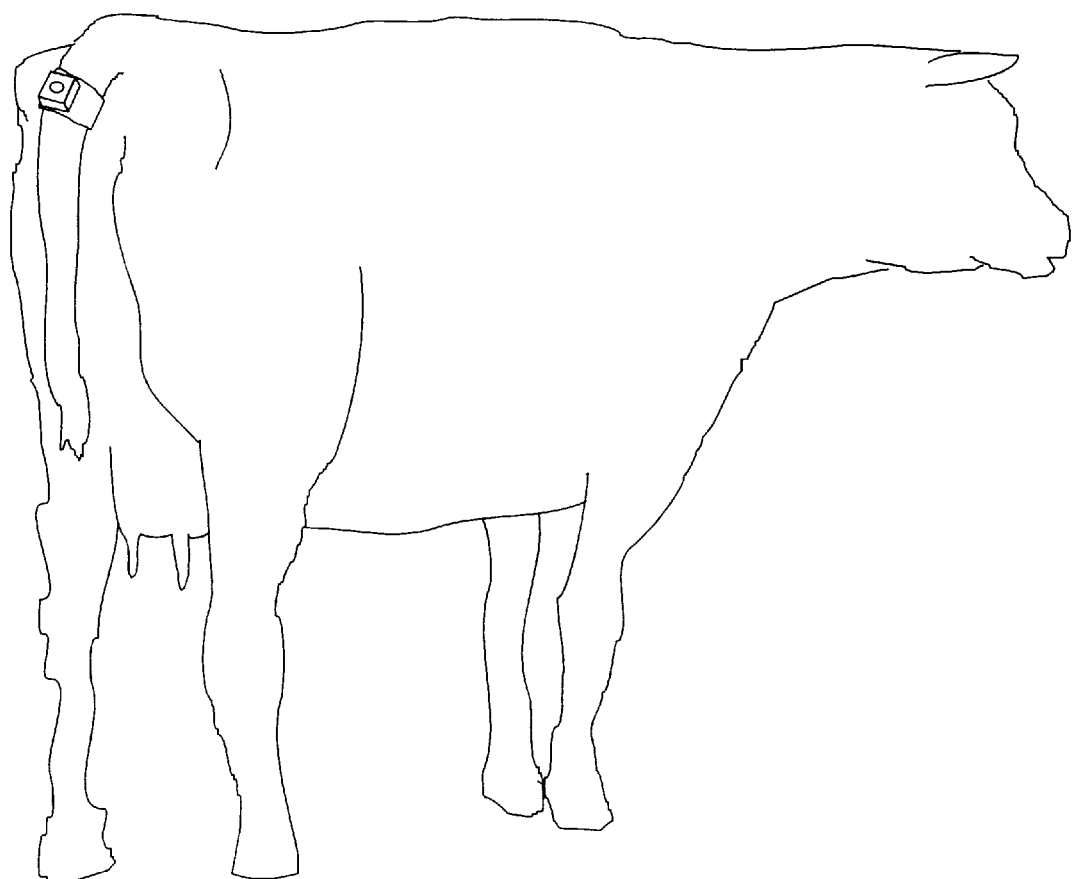
FIG. 6 illustrates where the removable sleeve of FIG. 1 could be placed on an animal to be monitored.

As illustrated in FIG. 6, the monitoring sleeve 25 is adjustably and removably attached to the animal's appendage by wrapping the sleeve 25 snugly around the appendage. The ends of the sleeve 25 are attached together via fastener strips 26 and 27, as illustrated in FIGS. 1–3. These fasteners 26 and 27 may be Velcro® strips for ease of fastening and unfastening. The upper end of the animal's tail is a preferred location for the removable sleeve for several reasons. One advantage is ease of use. The tail is easily accessible and the sleeve is simple to attach and remove. Furthermore, no incision is required in the animal, thus eliminating the chance of an infection occurring at the incision sites. Moreover, no insertion into a body cavity is required, thus eliminating the possibility of the device being dislodged or expelled. Because the upper end of the tail folds over the base of the animal, near its anus, the sensors will yield temperature measurements that are usefully accurate despite the fact that the sleeve is simply wrapped around the tail. An additional advantage to placing the sleeve around the animal's tail, as opposed to around its neck, is that a much smaller sleeve is required since a tail is much thinner than a neck.

Yet another advantage of the present invention is that because the instrument pack is easily removeable and can be separately inserted into the pouch of a new sleeve and thus easily reused. Similarly, if the instrument pack is somehow damaged or becomes inoperative, the sleeve can be reused by simply inserting a new instrument pack.

Figure 14:
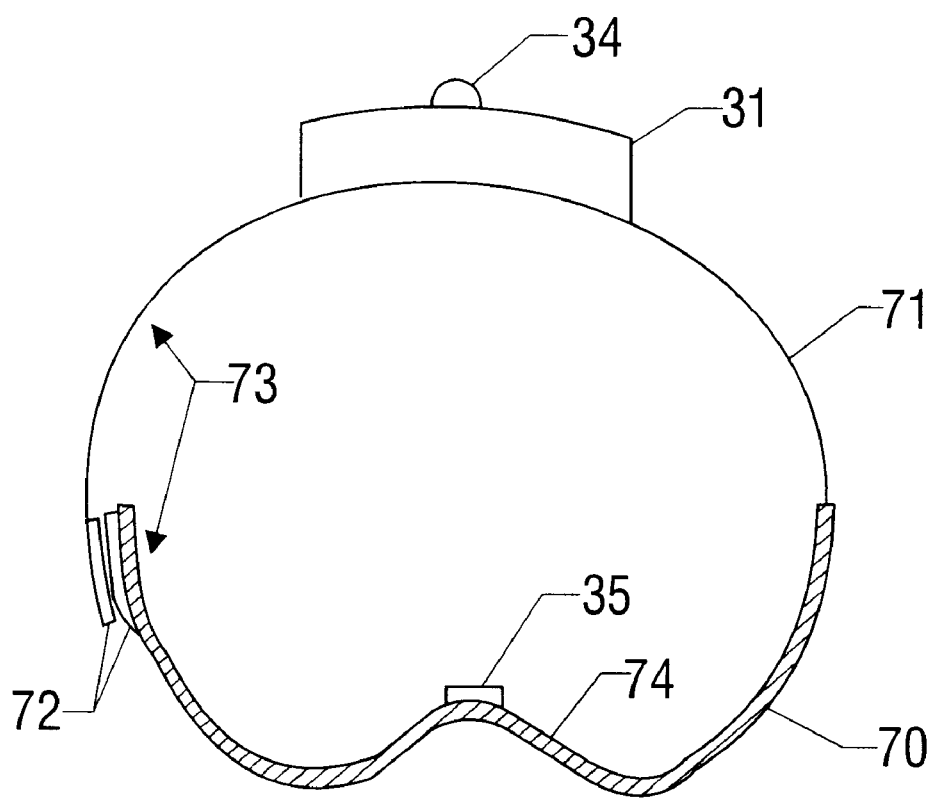
FIG. 14 illustrates a cross-sectional view of a sleeve design utilizing a plastic bottom having a "W" shape.

An alternative monitoring sleeve design that is useable in all of the embodiments of the present invention is illustrated in FIG. 14. This monitoring sleeve consists of a bottom portion 70 shaped like a shallow, rounded "W." This bottom portion 70 is preferably made of plastic and is slightly flexible. One or more biosensors 35 are located on the inner surface of the sleeve at the apex 74 of this "W"-shaped bottom portion 70. By placing the biosensors 35 at the top of the apex 74, the biosensors are pushed up into an intermuscular groove on the underside of the animal's tail and closer to an artery, thereby improving their ability to obtain accurate physiological measurements. Additionally, by resting within this intermuscular groove, the apex 74 helps anchor the sleeve and prevents it from rotating around the animal's tail. A medical adhesive may also be applied to the apex 74 in order to assist in keeping the biosensors positioned properly within the intermuscular groove. The top portion 71 of the sleeve is comprised of a stretchable fabric, such as elastic, that allows it to be stretched snugly around the animal's tail and be affixed to the bottom portion 70 by strips of Velcro® 72 or another fastening mechanism. On the top portion of the sleeve 71 is a pouch 31 and light 34 substantially similar to those described above in the other sleeve design. Both the top 71 and bottom 70 portions of the sleeve have a rubbery coating on their inner surfaces 73. This coating helps prevent the sleeve from sliding off of or rotating around the animal's tail. As with the previous sleeve design, the sleeve is preferably constructed of weather and excrement resistant materials and is lightly colored or reflective so as to minimize radiant solar heating.

Figure 5:
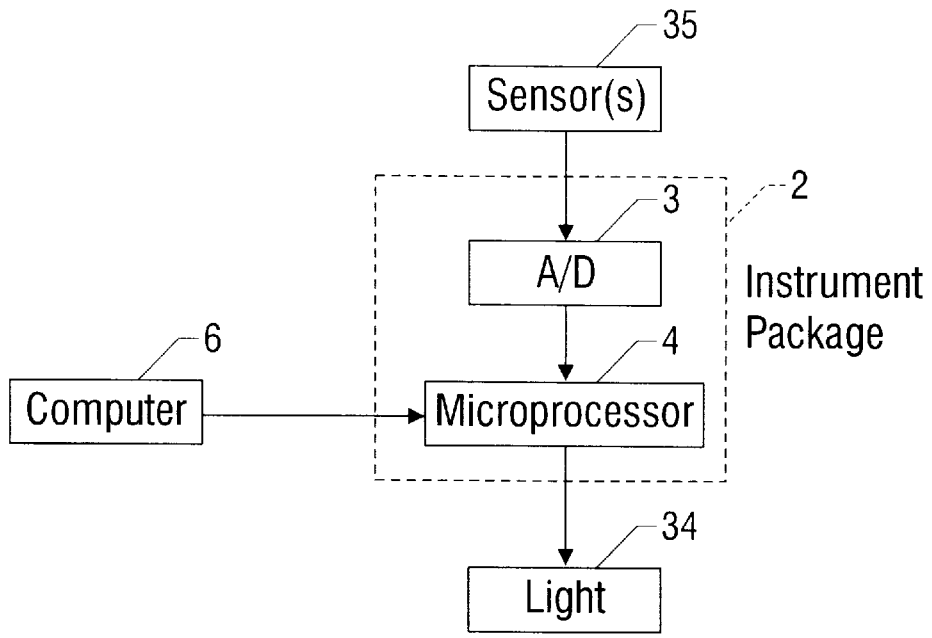
FIG. 5 is a block diagram for the first embodiment of the invention, illustrating how the monitoring sleeve activates an alarm if the animal's measured physiological parameter is outside a user-prescribed preset range.

FIG. 5 is a block diagram of the first embodiment of the present invention. The instrument pack 2 is inserted into the sleeve's pouch 31 and contains an analog to digital (A/D) converter 3 and a connected microprocessor 4. The one or more biosensors 35 connect to the instrument pack 2 via an electrical connector 60 (see FIG. 4). The one or more biosensors 35 are of the type to measure the animal's temperature and pulse rate. Other parameters, however, such as blood pressure, blood oxygen saturation, and skin electrical conductivity (as an indicator of stress) may also be measured by appropriate biosensors. Examples of biosensors include the "medical telesensors" developed by Oak Ridge National Laboratory for the Defense Advanced Research Projects Agency. The A/D converter 3 transforms the biosensor signals into binary signals and then sends them to the microprocessor 4.

The microprocessor 4 continually compares the biosensor readings to predetermined user-defined alarm activation criteria. There exists a wide variety of options in the selection of suitable alarm activation criteria. In a simple embodiment, the criteria may simply be when one or more of the measured physiological parameters exceed a specified threshold. Alternatively, in a slightly more sophisticated implementation, the alarm activation criteria may be when one or more of the measured physiological parameters falls outside of a pre-determined range for a pre-determined length of time. Finally, in a complex implementation, the alarm criteria may be defined as a function of multiple variables. For example, the alarm activation may be governed by a function of time and temperature such that if one or more of the measured physiological parameters is above a preset threshold, the time until the alarm activates is inversely proportional to the degree that the parameter exceeds that preset threshold. The rate of change of any or all of the measured physiological parameters may be used as a variable in the alarm activation function. The alarm thresholds may be selected such that they correspond with a value that is a certain number of standard deviations from the mean of the Gaussian distributions representing the normal distribution of values for the particular parameters being measured in the species of animal being monitored. The user defines the alarm activation criteria by programming the instrument pack 2 via a configuration computer 6 that uses a programming software package and communicates with the instrument pack 2 via a data port 62 (e.g., RS-232) as shown in FIG. 4. Alternatively, the instrument pack 2 itself may have a display 64 and a user interface 63 that enables the operator to directly enter the desired criteria without the need for a separate computer system.

If any of the animal's measured physiological parameters meet the pre-determined alarm criteria, the microprocessor 4 will activate an alarm by illuminating the light 34 located at the top of the pouch 31 of the monitoring sleeve (see FIGS. 1, 2, and 14). This visual alarm enables the pen rider to quickly identify those animals that have potential health problems.

Figure 7:
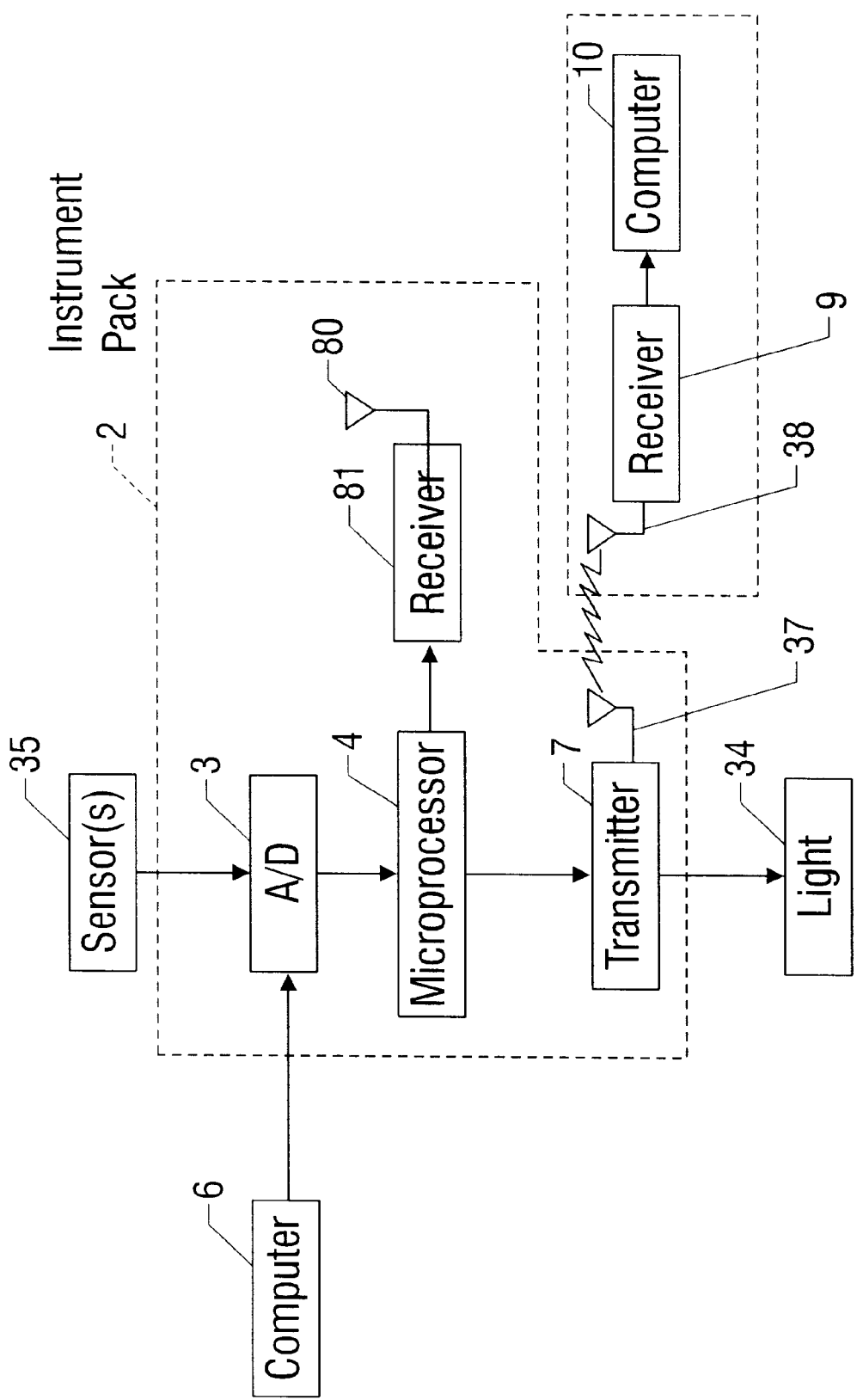
FIG. 7 is a block diagram for a second embodiment of the invention, which further includes transmitting the animal's physiological data to a base station.

FIG. 7 is a block diagram illustrating a second embodiment of the present invention. This second embodiment expands the capability of the animal monitoring system of the present invention by incorporating a transmitter 7 and antenna 37 in the instrument pack 2' to allow for the transmission of measured physiological data to a base station 8 established by the user. The same or substantially similar monitoring sleeve of FIGS. 1–3 and 14 can be used to house the instrument pack 2'. In fact, because the instrument pack is a separate unit that is inserted into the pouch of the monitoring sleeve, a feedlot operator has the flexibility of starting with a simple monitoring system such as that discussed and illustrated in FIG. 5 and then upgrading to a more sophisticated system, when convenient, by changing out the instrument pack and adding the base station.

The base station 8 comprises an antenna 38 feeding a radio receiver 9 interfaced to a computer 10. The microprocessor 4 uses the transmitter 7 and antenna 37 to send the animal's physiological data to the base station 8. Each animal would be provided with a unique identification number or other designation. In addition to activating the alarm light 34, the microprocessor 4 can be programmed to transmit biosensor readings and an alert message to the base station 8 when one or more of the measured parameters have met the pre-determined alarm activation criteria.

Alternatively, the microprocessor 4 may be programmed to transmit the biosensor data to the base station 8 at regular user-defined periodic intervals. However, if the animal's temperature, pulse rate, or other measured physiological parameter meets the pre-determined alarm activation criteria, then the microprocessor 4 transmits an unscheduled alert broadcast to the base station 8 in order to immediately notify the feedlot operator or pen rider of a problem in addition to activating the alarm light 34. The base station also includes software that informs the operator as to which pen the animal is located so that the pen rider can proceed to that pen and quickly identify the sick animal by locating the illuminated alarm light 34. The base station 8 software is able to identify the proper pen by correlating the animal's transmitted identification number with a database containing the pen assignments for each herd or animal.

In addition, by recording the periodic reports made by the instrument packs, the base station 8 can accumulate a physiological database for each animal. This accumulated data allows the feedlot operator to track changes in the physiological parameters of each animal over a period of time and to use the data to determine when certain animals are in estrus period, which animals suffer repeated illnesses, and how environmental or other factors influence the health of the livestock. The uses to which a feedlot operator could put the transmitted physiological data for each animal are mostly limited by the software programs that can be installed on the base station's computer 10.

As a practical matter, it is desirable to have a single channel base station receiver 9 in order to minimize costs. However, the feedlot operator may be monitoring several thousand head of cattle at the same time thereby posing a frequency congestion problem if the instrument packs have been programmed to provide regular periodic reports of each animal's physiological parameters. To minimize this problem, each instrument pack's transmitter 7 can be designed to randomly jitter the transmit time around the selected reporting interval so as to randomize the transmissions temporally and thus minimize the possibility of overlapping broadcasts being received by the base station.

Alternatively, the data link system comprising the transmitter 7 and the base station receiver 9 may use Time Division Multiple Access (TDMA) or Code Division Multiple Access (CDMA) techniques to accomplish the same result. Such techniques are well known to one of ordinary skill in the art. The feedlot operator may wish to have several single channel base station receivers 9, each operating on a separate channel and connected to one or more base station computers 10. With such a configuration, the feedlot operator can assign all cattle belonging to a particular owner a different frequency and thus monitor each herd separately.

The microprocessor 4 of the instrument pack 2' is pre-programmed by the user through the configuration computer 6 and its programming software package. As a practical matter to minimize costs, the functions of configuration computer 6 can be implemented by the base station 8 computer 10 thus requiring only a single computer as opposed to two. With the computer connected to data port 62 (see FIG. 4), the user can define the alarm activation criteria which triggers the transmission of an alarm signal to the base station 8 and the illumination of the alarm light 34. This programming capability gives the user the flexibility of changing the alarm criteria to compensate for different types of animals as well as ambient conditions which may affect temperature readings. The user can also program other parameters such as the identification number for the animal, the frequency that the transmitter 7 should use, and the interval to use between transmissions if periodic reporting is desired. Alternatively, the instrument pack's 2' configuration parameters can be input via a display 64 and user interface 63 shown in FIG. 4, thus eliminating the need for a separate external computer to configure the instrument pack 2'.

An alternative implementation of the second embodiment incorporates an antenna 80 and receiver 81 in the instrument pack 2. The receiver 81 is operatively connected to the microprocessor 4. The addition of the receiver allows the feedlot operator to program the instrument pack over-the-air by using a remote computer attached to a transmitter (not shown). The feedlot operator can use the computer and transmitter to conveniently program the alarm activation criteria, the animal's identification number, the instrument pack's transmitter frequency, the instrument pack's reporting interval, the location reporting mode, or any other user programmable parameters. In this version of the second embodiment, each instrument pack has its own identification number, which may or may not be the same as the animal's identification number, so that it can be selectively and individually programmed by the remote computer and transmitter.

Another useful aspect of this version of the second embodiment is that it makes it easy for the feedlot operator to locate a sick animal while at the same time conserving instrument pack battery power. For example, if an animal becomes ill and the alarm activation criteria are met, the instrument pack will transmit an alert signal to the base station. The feedlot operator is then faced with the task of going out to the pens to locate the sick animal among several thousand head of cattle. In these situations, it may not be desirable to have the instrument pack automatically activate the alarm light on the sleeve because there may be delays before the feedlot operator can go scout for the animal, and these delays may drain the instrument pack's batteries. By using a small portable computer (e.g. a laptop or palm size) and an attached transmitter (not shown), the feedlot operator can, at his convenience, go out to the pen area and transmit a signal to the instrument pack's receiver that instructs the microprocessor to illuminate the alarm light on the sleeve of the sick animal. This enables the feedlot operator to easily locate the animal while at the same time preserving battery power by only illuminating the alarm light when the feedlot operator is ready to go look for the sick animal.

In addition to monitoring the animal's temperature, pulse rate and/or other physiological parameters, it is very beneficial to have some indication of the animal's feed and/or water intake. A third embodiment of the monitoring system of the present invention provides the ability to monitor the geographic location of the animal and determine the frequency and amount of time spent in or near the feed bunks and water troughs. In order to effectively practice this third embodiment, the feedlot layout should be mapped and digitally stored. That is, the geographic coordinates of the feed bunks and water troughs should be predetermined and stored into a database or look-up table for reasons that will become apparent with the following discussion. With the exception of the addition of the position determination system, the third embodiment comprises essentially the same components and options as the second embodiment described above.

Figure 8:
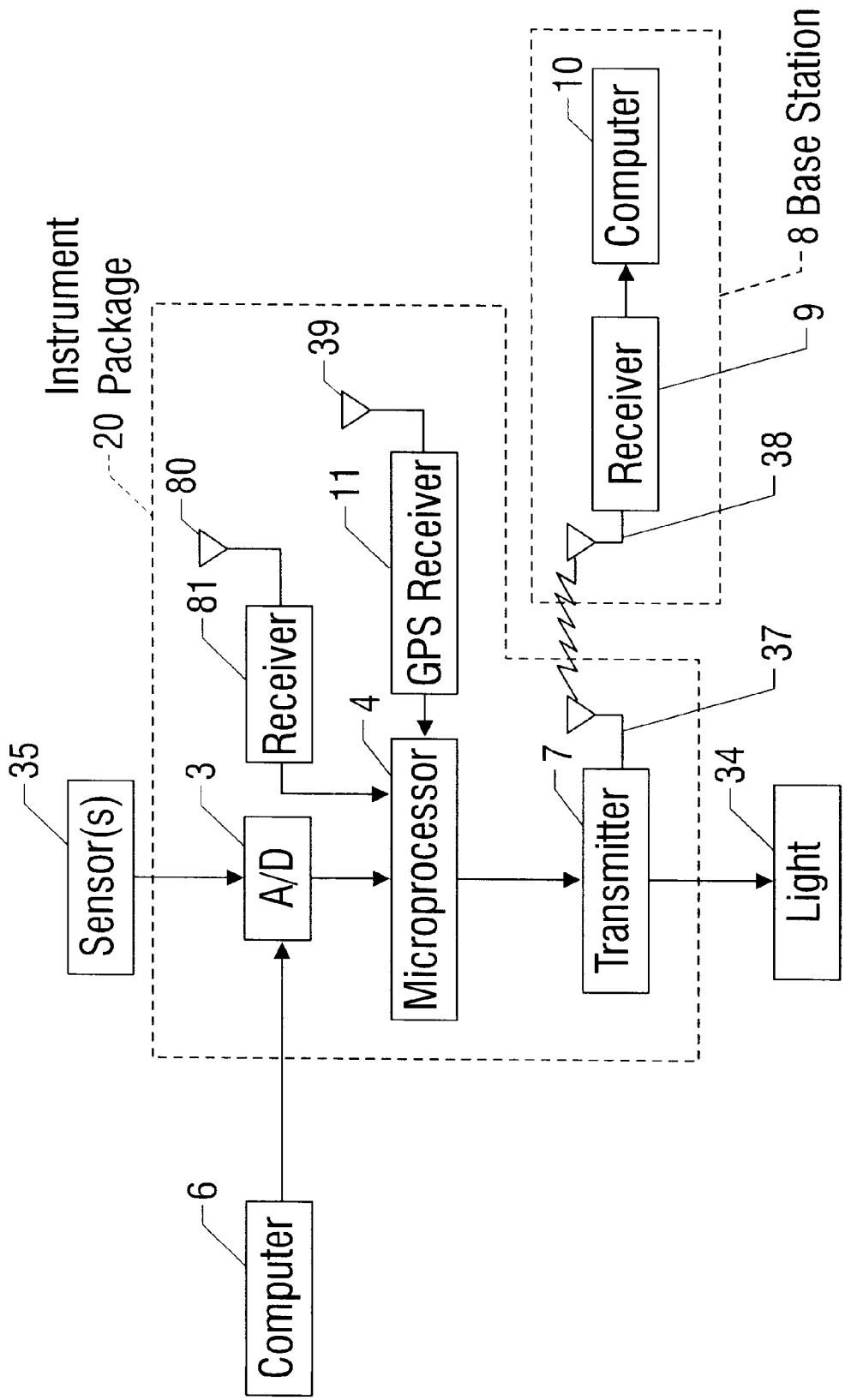
FIG. 8 is a block diagram of one implementation of a third embodiment of the invention, which further includes using GPS technology to monitor the animal's location.

FIG. 8 is a block diagram illustrating one implementation of the third embodiment of this invention. The instrument pack 20 comprises essentially all the components of the second embodiment described above but also includes a small global positioning system (GPS) receiver 11 and built in patch antenna 39 to determine the animal's location. By using a configuration computer 6, a built-in display 64 and user interface 63, or over-the-air programming, the instrument pack 20 can be programmed for several different reporting modes.

One alternative is to have the instrument pack 20 make periodic reports of the animal's location. This would be the most likely option when the user has also programmed the instrument pack 20 to make regular periodic reports of the animal's physiological parameters. With this option, the base station 8 would determine when and for how long each animal has been at a feed or water trough by comparing each animal's position reports to a digital map of the feedlot area.

An additional option is to program the instrument pack 20 to make position reports to the base station 8 only when an animal enters or exits a feed or water trough area. This option helps conserve power by minimizing use of the instrument pack's 20 transmitter 7. Frequency congestion is also reduced because fewer reports are being made in comparison with the periodic reporting option. To implement this option, the feedlot's digital map would need to be loaded into the instrument pack 20 via over-the-air programming or via the instrument pack's data port 62 and the configuration computer 6 so that the instrument pack knows when the animal has entered and left a feed or water trough area.

Another alternative is to program the instrument pack 20 to maintain a log for the animal recording how long the animal was at the feed bunks or water troughs. This log would then be downloaded to the base station 8 after a pre-defined interval (e.g., daily). For this option to work, the digital feedlot map would again have to be programmed into the instrument pack 20 via the configuration computer 6 or over-the-air. In versions of the third embodiment that include a receiver 81 connected to the microprocessor 4, the microprocessor can be instructed at any time to transmit its data log to the base station 8. This is accomplished by using a transmitter (not shown) to send command instructions to the microprocessor to initiate the download of the log.

With any of these reporting options, the software in the base station computer 10 can track each animal's feed and water consumption and alert the feedlot operator in the event that an animal is not feeding or drinking sufficiently.

To determine a location using GPS, the receiver 11 ordinarily needs to obtain ranging signals from four or more of the currently existing twenty-four orbiting GPS satellite vehicles (SVs). For civil users (e.g., non-military) this provides horizontal positioning accuracy of 100 meters (95%). The accuracy would be better (i.e., 30 meters, 95%) but for the Department of Defense's intentional degradation of the signal to civil users for national security reasons via the Selective Availability (SA) program. Although positioning accuracy would be degraded, signals from only three GPS SVs are necessary in order to provide a 2-D horizontal position if the receiver makes an assumption for altitude (e.g., average radius of Earth, last known altitude, etc.).

Figure 9:
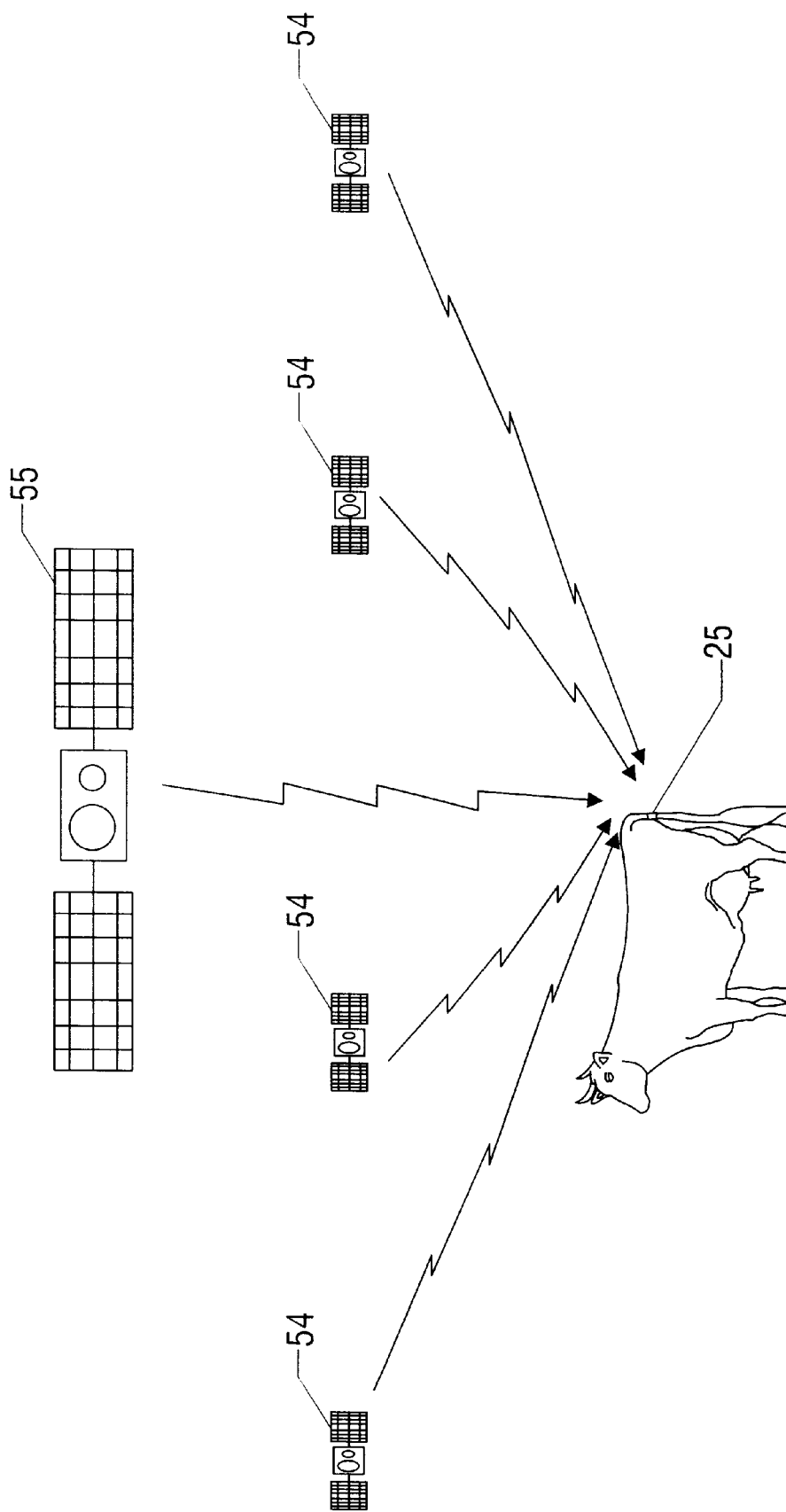
FIG. 9 illustrates the use of the FAA's Wide Area Augmentation System to improve the position determination accuracy of the animal when using GPS.

In order to achieve sufficient positional accuracy for feedlot applications, the GPS receiver 11 in the instrument pack 20 can be augmented by the use of signals from the Federal Aviation Administration's (FAA) Wide Area Augmentation System (WAAS). Although primarily designed to assist in the navigation of commercial aircraft, the WAAS signals are available to all interested users. FIG. 9. illustrates how the animal's location is determined using WAAS. The GPS receiver in the removable sleeve 25 receives basic GPS ranging signals from four or more GPS SVs 54. In addition, the GPS receiver also receives a WAAS correction signal from an Inmarsat III geostationary satellite 55. This signal provides the GPS receiver with correction data to remove errors caused by atmospheric delay, ephemeris errors, selective availability, and other sources. The WAAS signal uses the same L1 frequency (1575.42 MHz) that the GPS SVs use, thus simplifying the design of the GPS receiver and keeping costs down while providing improved accuracy performance.

Figure 10:
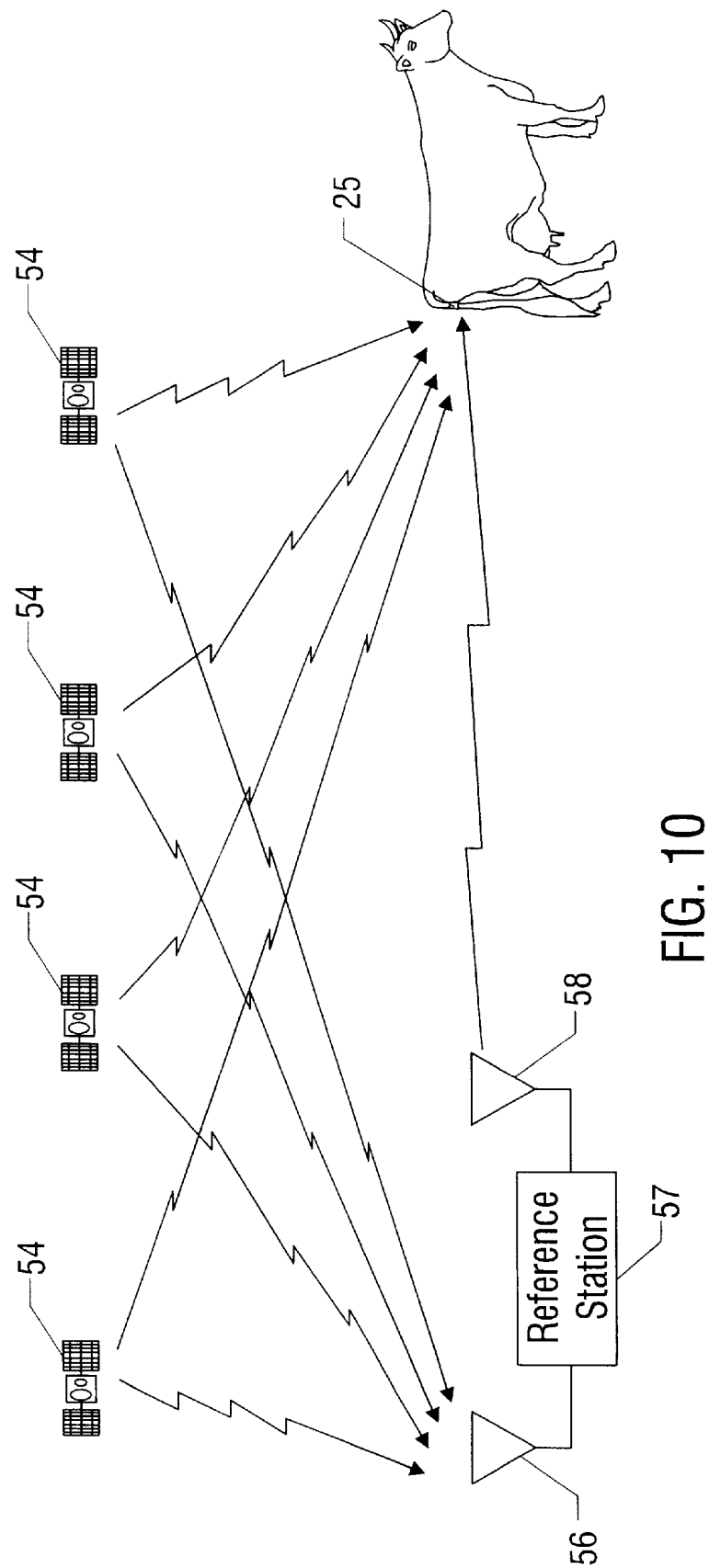
FIG. 10 illustrates the use of a local areas differential GPS system to improve the position determination accuracy of the animal when using GPS.

Alternatively, the GPS receiver may be augmented by a local area differential GPS system that broadcasts locally-computed differential corrections to all of the sleeve-mounted GPS receivers in the feedlot area. This technique is illustrated in FIG. 10. In this implementation, the GPS receiver in the sleeve 25 receives GPS ranging signals from a minimum of four GPS SVs 54. These GPS signals are also received by the antenna 56 of a ground reference station 57. The reference station computes its location using the GPS signals and compares this GPS-derived location to its actual surveyed location. The difference between these two locations represents the total GPS error. The reference station then broadcasts correction signals via antenna 58 to all of the sleeve-mounted GPS receivers in the feedlot area. The GPS receivers are then able to use these correction signals to remove the GPS error components and substantially improve their location determination accuracy.

Alternatively, instead of using a GPS system, a tag-based system can be used to monitor the animals' locations by causing a signal to be transmitted to the base station whenever an animal bearing a tag passes near a sensor mounted adjacent to or near a feed bunk or water trough. Again, such information would provide the frequency and amount of time the animal spends near the bunks and troughs and serves as a useful approximation of the animal's feed and water consumption.

Figure 11:
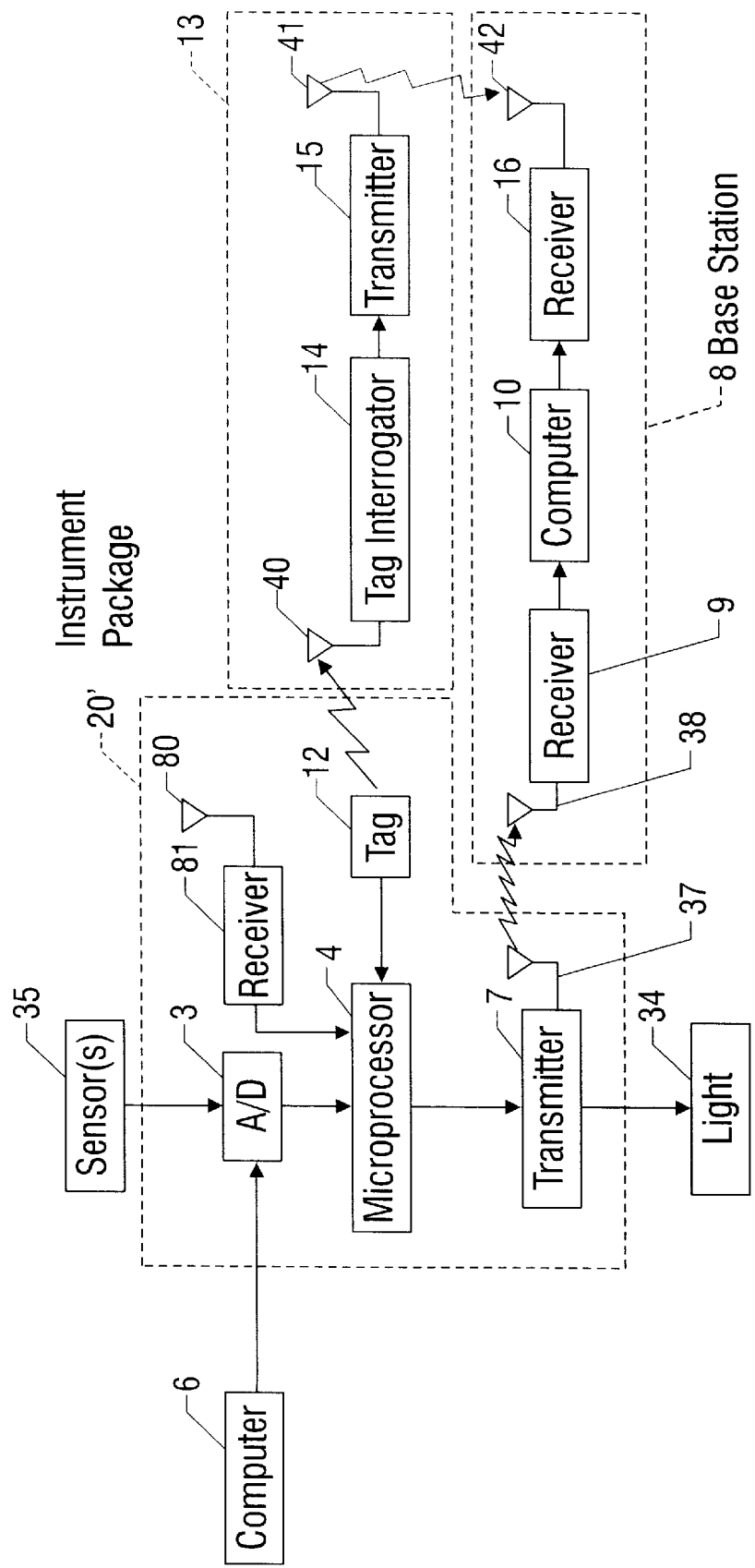
FIG. 11 is a block diagram of an alternative implementation of the third embodiment of the invention, wherein radio frequency tags encoded with the animal's identification number are read by tag interrogators located adjacent to the feed and water troughs and the information is relayed to the base station.

As shown in FIG. 11, a tag-based system would comprise of a tag interrogator station 13 having an interrogator coil 40, an antenna 41, interrogator circuitry 14, and a transmitter 15. The final component, the tag 12 itself, is contained on or within the instrument pack 20' and interfaces with the microprocessor 4. The microprocessor 4 uses the interface to program the tag 12 with the animal's ID number as well as other data such as the animal's physiological parameters. The tag 12 itself comprises a small antenna (not shown) together with an integrated circuit (not shown) which contains the power on/reset circuitry, command decode logic which determines how the tag responds to information received from the interrogator 14, and memory. The tag 12 may be passive and derive its energy from the electromagnetic field generated by the interrogator antenna/coil 40, or the tag 12 may be actively powered by the instrument pack's power source for improved range. Tag/interrogator systems such as described above are commercially available from numerous manufacturers (e.g., Raytheon, Gemplus, Omron Electronics, Micron Communications, and ID Technologies).

Each water trough and/or feed bunk has its own tag interrogator station 13. When the animal is near a feed bunk or water trough, the tag is energized by a radio frequency field generated by the tag interrogator coil 40 and acquires sufficient energy to power its circuitry. Once energized, the tag is able to influence the field generated by the interrogator coil 40 to allow it to transfer the animal's identification number to the interrogator 14. The interrogator 14 then uses a transmitter 15 and antenna 41 to relay the information to an antenna 42 and receiver 16 at the base station 8. Alternatively, the tag interrogator itself 14 may use a cable (not shown) between itself and the base station 8 to send the data. Assuming that such a cable can be practicably run between the tag interrogator and the base station at a particular feedlot, it provides the advantage of eliminating the transmitter 15, receiver 16, and antennas 40 and 41, thus helping to lower the overall system costs. Alternatively, an inverse implementation (not shown) is also possible whereby the instrument pack 20' sends the animal's location to the base station 8 via its transmitter 7 and antenna 37. In this inverse implementation, the tag 12 senses the radio frequency field generated by a tag interrogator coil 40 and sends a signal to the microprocessor 4 indicating which interrogator coil 40 the animal is standing near. Each tag interrogator 14 would modulate its radio frequency field with a unique identification number that the tag 12 receives and relays to the microprocessor 4 for transmission to the base station 8. The advantage of this approach is that it eliminates the need for the tag interrogator station's 13 transmitter 15 and antenna 41, it eliminates the need for the base station's receiver 16 and antenna 42, and finally it also eliminates the need to run cables from all of the interrogator stations 13 to the base station 8.

As discussed in the previous embodiment of the present invention, the location information provided to the base station computer allows the feedlot operator to monitor the food or water intake of each individual animal by using total time at the feed bunks or water troughs as a proxy for food or water consumption respectively. This can assist the operator in identifying sick or injured animals that are unable or unwilling to properly nourish themselves. Additionally, the feedlot operator can use the information to allocate feed costs to individual cattle owners based upon their herd's feed consumption.

Figure 12:
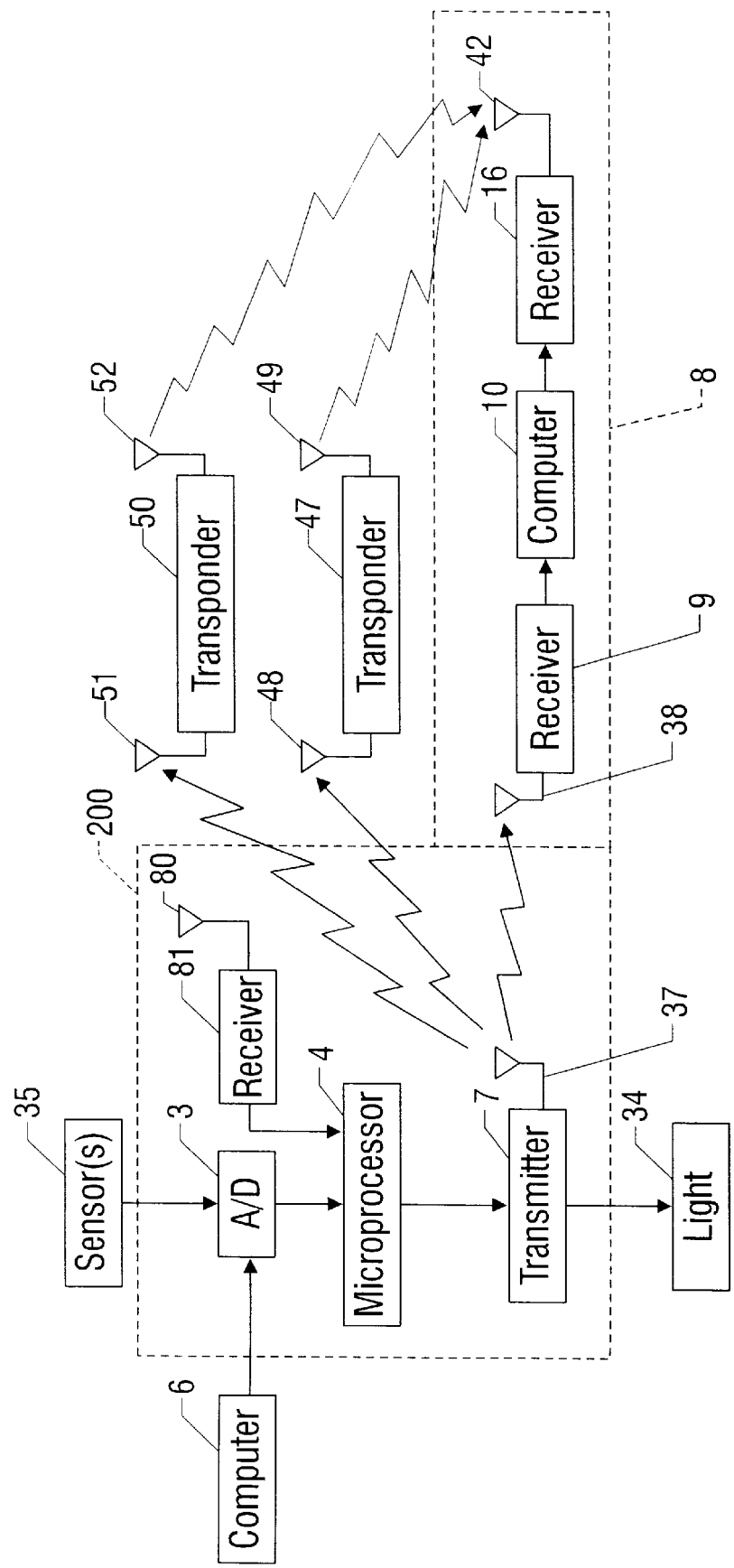
FIG. 12 is a block diagram of an alternative implementation of the third embodiment of the invention, wherein a time difference of arrival system is used to determine a particular animal's location within the feedlot.
Figure 13:
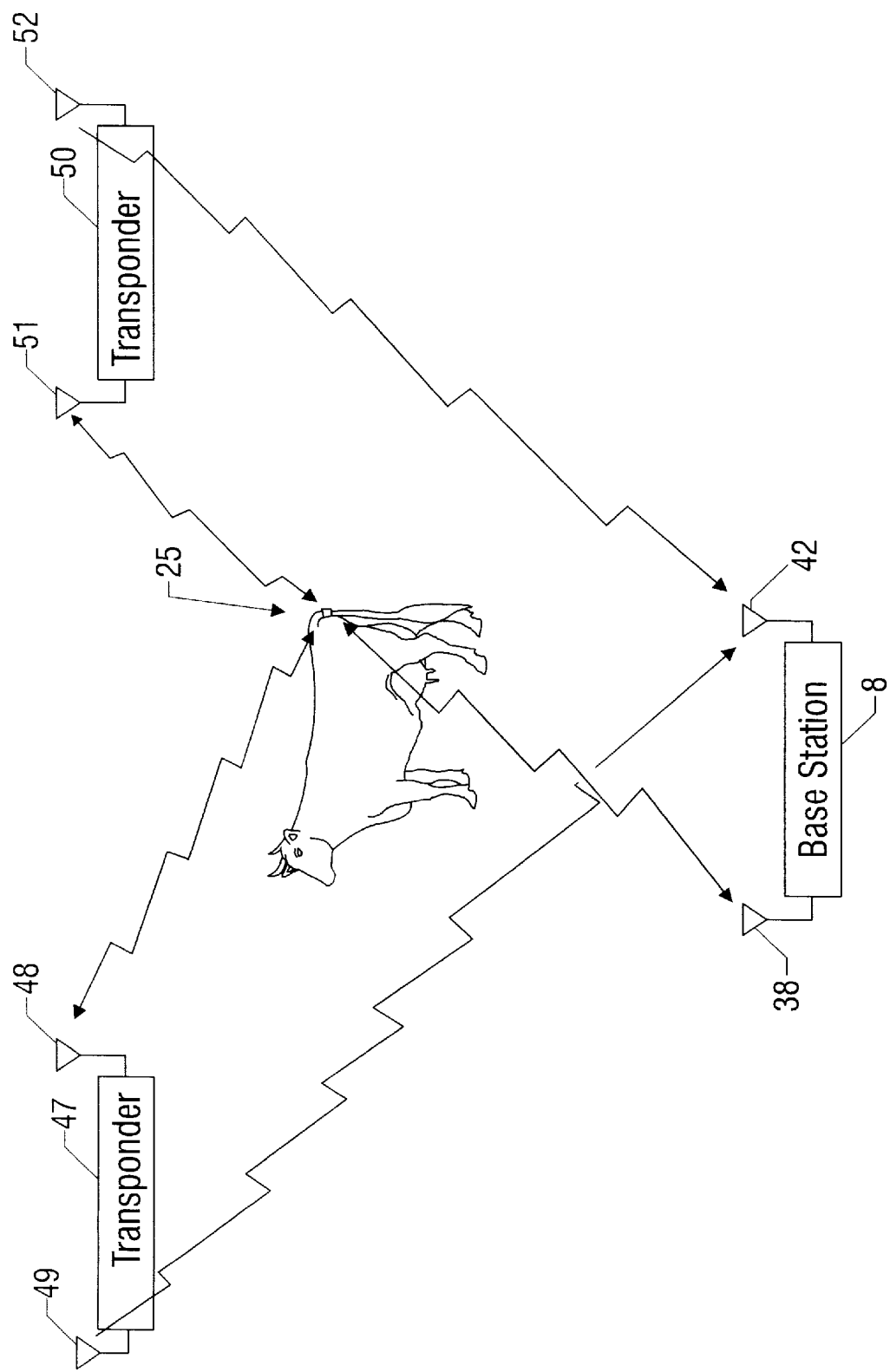
FIG. 13 illustrates how the time difference of arrival alternative would be implemented in the feedlot area.

A time difference of arrival (TDOA) technique is yet another way of implementing the third embodiment of the present invention and is illustrated in FIGS. 12 and 13. This implementation uses two transponders 47 and 50 with antennas 48, 49, 51, and 52, respectively, and a base station with antennas 38 and 42, respectively, and receivers 9 and 16. The two transponders 47, 50 and the base station 8 are all widely separated from each other, preferably in the form of an equilateral triangle, and precisely surveyed and installed in the vicinity of the feedlot. When the transmitter 7 in the instrument pack 200 reports the animal's physiological parameters to the base station 8, the transmission is received by the base station antenna 38 as well as the antennas 48 and 51 of the transponders 47 and 50, respectively. The transponders may be powered by AC electrical power, batteries, or solar cells. When the transponders receive a transmission from the instrument pack, they relay the transmission to the base station 8 along with an identifying number or code to indicate which relayed transmission is coming from which transponder. Alternatively, if the transponders are time synchronized with the base station, they can simply transmit to the base station the specific time, preferably with accuracy within the nanosecond range, as to when they received a specific transmission from a given animal along with the animal and transponder identification codes. The transponders transmit information to the base station via antennas 49 and 52. This information is received by an antenna 42 and receiver 16 at the base station. Alternatively, the transponders may be hard wired to the base station via electrical cables (not shown) so as to eliminate some of the radio components and reduce system costs. The base station uses the arrival time information at antennas 38, 48, and 51 to calculate a specific animal's position using time difference of arrival techniques. By continually monitoring the animal's location in this way, the software in the base station computer can determine when and for how long a particular animal has been at the feed bunks and/or water troughs and thus approximate its feed and/or water consumption.

This third embodiment of the present invention provides the frequency and amount of time a particular animal has spent within the feed and water zones on any given day, week, month or any preselected monitoring period, regardless of whether a GPS-based, a tag-based, or TDOA-based system is used. Since the level at which an animal eats and drinks serves as an indicator of the animal's health, the user will have yet another tool to monitor the animals maintained at the feedlot. The combination of monitoring the animal's physiological parameters, such as its temperature and pulse rate, with its frequency of food and water intake will help the feedlot operator to identify the sick animal quickly before the sickness substantially progresses and potentially spread to the other animals.

The foregoing description and illustrations contained herein demonstrate many of the advantages associated with the present invention. In particular, it has been revealed that a cost effective and simple to use animal monitoring system is provided through the use of a removable sleeve containing requisite monitoring instrumentation. The present invention offers significant improvements over the prior art in that it does not require implanting sensors into the animal thus eliminating the risk of causing an infection at an implant site. An added benefit is that the instrumentation is removable from the sleeve and is thus reusable. Once the particular animal no longer requires monitoring, the sleeve can simply be removed and the monitoring instruments removed therefrom. The sleeve can then be discarded while the instrument pack can be inserted into a new sleeve to be placed onto a different animal to be monitored.

Moreover, the monitoring system is flexible, easily adaptable, and upgradeable to meet the user's needs and budget. The contents of the instrument pack depend upon the particular embodiment of the invention utilized and can be tailored to suit the user's requirements. For those users who only desire to invest in a basic temperature and pulse rate monitoring system, the main instruments needed are a biosensor and a microprocessor to process the signals from the biosensor and to activate an alarm, such as a light, when the animal's temperature and/or pulse rate are out of a desired preselected range. If the user, however, wants to record this information and monitor the animal from a base station, a transmitter can be added to the basic instrument pack to transmit the signals from the biosensor and microprocessor to the base station. The operators at the base station will be alerted when the signals are received that a particular animal needs to be examined for potential health problems. The base station can also have a computer system set up to receive these transmitted signals and store the information into a database. This database can then be manipulated through various computer programs that the user can design to yield useful information, such as how often a particular animal registers unusual temperature and/or pulse rate, how many animals exhibit these symptoms within a defined time period, which type and breed of animals are prone to sickness, and whether there are any patterns that can be observed. This type of information can be very useful to the feedlot operator and is made possible through use of the present invention's adaptable monitoring system.

Yet another advantage of the present invention is that the feeding and watering habits of specific animals can also be monitored. This embodiment of the invention would require greater initial monetary investment because the feedlot must be mapped and digitally stored, but substantially more information can be obtained and used. The instrumentation package contained within the sleeve would be expanded to include a GPS transmitter so that location of the animal would be transmitted to the base station whenever the animal enters particular zones, such as feeding or watering zones, on the feedlot. Then, as the animal leaves the zone, another location signal is transmitted to the base station so that the operator can determine how long an animal spends in the feed and/or water zone and how often. If an animal fails to enter into either zone with sufficient frequency and duration, the operator will be alerted that a problem may exist with that animal and take immediate remedial action. Again, all the transmitted information can be processed and stored within a database so that it can be manipulated to give useful information. For example, the feedlot operator can have a computer program designed to use this information to calculate an approximation of how much feed and water are consumed by a particular animal for accounting purposes. The information can also be used to determine which feed and water zones are most frequented by animals to properly stock those areas. The information can also be used to project when particular cattle will reach ideal weight based upon their feed consumption pattern. Again, all these applications may be possible through the use of the monitoring system of the present invention.

Thus, it is apparent that there has been provided, in accordance with the invention, an expandable animal monitoring system that substantially meets the need and advantages set forth previously. Although the invention has been described and illustrated with reference to specific embodiments thereof, it is not intended that the invention be limited to these illustrative embodiments. Those skilled in the art will recognize that modifications and variations can be made without departing from the spirit of the invention. For example, the biosensors may extend substantially across the length of the sleeve so that any inadvertent twisting of the sleeve on the animal's appendage will not cause the biosensors to lose contact with the warmest part of the animal. Additionally, for those animals where it is not practicable to wrap the sleeve around their tails, other appendages may be used. It is also important to note that the present invention is not limited in any way to monitoring only cattle, but may be adapted to monitor other animals, even animals set to roam in the wild. Therefore, it is intended that this invention encompass all such variations and modifications falling within the scope of the appended claims.

What is claimed is:

1. An animal monitoring system, comprising:
    a sleeve capable of being removably attached to an appendage of an animal to be monitored, the sleeve having an inner surface adapted to be adjacent to the surface of the appendage;
    a biosensor attached to the inner surface of the sleeve for measuring at least one physiological parameter of the animal;
    a pouch formed in the sleeve; and
    an instrument pack for insertion into the pouch, the instrument pack having a microprocessor operatively connected to the biosensor for activating an alarm when the measured physiological parameter of the monitored animal meets predetermined alarm activation criteria.

2. The animal monitoring system of claim 1, wherein the appendage of the animal is its tail, and wherein the sleeve is configured to be attached to the upper end of the animal's tail.

3. The animal monitoring system of claim 1, wherein the biosensor senses at least one of the animal's temperature, pulse rate, blood pressure, blood oxygen saturation, and skin conductivity.

4. The animal monitoring system of claim 1, wherein the inner surface of the sleeve is a non-slip surface.

5. The animal monitoring system of claim 1, wherein the sleeve is padded with a thermally insulating material.

6. The animal monitoring system of claim 1, wherein the sleeve has an outer surface that is light reflective.

7. The animal monitoring system of claim 1, wherein the sleeve has a fastener for adjustably and removably securing said sleeve to the appendage of the animal.

8. The animal monitoring system of claim 7, wherein the fastener is a loop and hook type fastener.

9. The animal monitoring system of claim 1, wherein the sleeve comprises both top and bottom portions.

10. The animal monitoring system of claim 9, wherein the bottom portion comprises a rounded "W"-shape with one or more biosensors affixed to its apex.

11. The animal monitoring system of claim 10, wherein the bottom portion of the sleeve is comprised of plastic.

12. The animal monitoring system of claim 9, wherein the top portion comprises a stretchable fabric.

13. The animal monitoring system of claim 1, further comprising an electrical interface for operatively connecting the microprocessor to a remote computer.

14. The animal monitoring system of claim 1, wherein the instrument pack has a user interface for programming the alarm activation criteria.

15. The animal monitoring system of claim 1, wherein the alarm activated by the microprocessor comprises a light.

16. An animal monitoring system, comprising:
    a sleeve capable of being removably attached to an appendage of an animal, the sleeve having an inner surface adapted to be adjacent to the surface of the appendage;
    one or more biosensors attached to the inner surface of the sleeve for sensing one or more physiological parameters of the animal and for providing one or more signals representative of the one or more physiological parameters being sensed;
    a pouch formed in the sleeve; and
    an instrument pack for insertion into the pouch, the instrument pack having a microprocessor operatively connected to the one or more biosensors for receiving the one or more signals from the one or more biosensors and activating an alarm in response thereto when pre-determined alarm activation criteria have been met;
    a transmitter operatively connected to the microprocessor for transmitting signals identifying the animal and providing data relating to the one or more physiological parameters being sensed by the biosensors; and
    a base station spaced from the animal for receiving the signals from the transmitter.

17. The animal monitoring system of claim 16, wherein the microprocessor is programmed to transmit the animal's physiological data to the base station at regular periodic intervals.

18. The animal monitoring system of claim 17, wherein the transmitter randomly jitters its broadcasts around the regular periodic interval to minimize interference caused by overlapping broadcasts.

19. The animal monitoring system of claim 16, wherein the microprocessor transmits an alert signal to the base station when the alarm activation criteria have been met.

20. The animal monitoring system of claim 16, further comprising a receiver operatively connected to the microprocessor.

21. The animal monitoring system of claim 20, wherein the microprocessor can be remotely programmed with one or more of the following: the alarm activation criteria, the animal's identification number, the instrument pack's identification number, the instrument pack's transmitter frequency, the instrument pack's reporting interval, or the reporting mode.

22. The animal monitoring system of claim 20, wherein the instrument pack includes an alarm light connected to the microprocessor, and wherein the microprocessor can be remotely instructed to illuminate the alarm light via a signal received by the receiver.

23. The animal monitoring system of claim 16, wherein the transmitter and the base station communicate using Code Division Multiple Access (CDMA) radio techniques.

24. The animal monitoring system of claim 16, wherein the transmitter and the base station communicate using Time Division Multiple Access (TDMA) radio techniques.

25. An animal monitoring system, comprising:
- a sleeve capable of being removably attached to an appendage of an animal, the sleeve having an inner surface;
- one or more biosensors for sensing one or more physiological parameters of the animal, the biosensors being coupled to the inner surface of the sleeve;
- a microprocessor operatively connected to the biosensors for activating an alarm when pre-determined alarm activation criteria have been met;
- a base station;
- a transmitter operatively connected to the microprocessor for transmitting signals to the base station identifying the animal and providing data relating to the one or more physiological parameters as sensed by the biosensor; and
- a location determination system for measuring when and how long a particular animal is at a feed bunk or water trough.

26. The animal monitoring system of claim 25, wherein the location determination system comprises a GPS receiver.

27. The animal monitoring system of claim 26, wherein the GPS receiver utilizes WAAS corrections to enhance its position determination accuracy.

28. The animal monitoring system of claim 26, wherein the GPS receiver utilizes locally computed differential GPS corrections to enhance its position determination accuracy.

29. The animal monitoring system of claim 25, wherein the transmitter broadcasts the animal's location to the base station at regular user-defined periodic intervals.

30. The animal monitoring system of claim 25, wherein the transmitter broadcasts the animal's location to the base station when the animal has moved near a feed bunk or water trough.

31. The animal monitoring system of claim 25, wherein the microprocessor maintains a log of when or for how long the animal was at a feed bunk or water trough and the transmitter broadcasts information in the log to the base station at regular user-defined periodic intervals.

32. The animal monitoring system of claim 25, further comprising a receiver operatively connected to the microprocessor.

33. The animal monitoring system of claim 32, wherein the microprocessor can be remotely programmed with one or more of the following: the alarm activation criteria, the animal's identification number, the instrument pack's identification number, the instrument pack's transmitter frequency, digital map data, the instrument pack's reporting interval, or the reporting mode.

34. The animal monitoring system of claim 32, wherein the instrument pack includes an alarm light connected to the microprocessor, and wherein the microprocessor can be remotely instructed to illuminate the alarm light via a signal received by the receiver.

35. The animal monitoring system of claim 32, wherein the microprocessor maintains a log of when or for how long the animal was at a feed bunk or water trough.

36. The animal monitoring system of claim 35, wherein the microprocessor can be remotely instructed to transmit its log to the base station by sending a radio signal to its connected receiver.

37. The animal monitoring system of claim 25, wherein the location determination system comprises:
- a data tag operatively connected to the microprocessor; and
- one or more tag interrogators.

38. The animal monitoring system of claim 37, wherein at least one tag interrogator is operatively connected to a transmitter for broadcasting the animal's identity and location to the base station.

39. The animal monitoring system of claim 37, wherein the one or more tag interrogators communicates an animal's identity and location to the base station via an electrical data cable.

40. The animal monitoring system of claim 25, wherein the location determination system comprises:
- two or more transponders that are spaced apart from each other and whose locations are surveyed;
- a base station that is spaced apart from the two or more transponders and whose location is surveyed, the base station having a receiver and a computer; and
- a software program in the computer at the base station that uses differences in a signal's arrival time at the base station and the transponders to calculate an animal's location.

41. The animal monitoring system of claim 40, wherein the transponders relay instrument pack transmissions or communicate the arrival times of such transmissions to the base station via radio transmitters operatively connected to the transponders to a radio receiver operatively connected to the base station.

42. The animal monitoring system of claim 40, wherein the transponders relay instrument pack transmissions or communicate the arrival times of such transmissions to the base station via electrical cables.

* * * * *